United States Patent
Apelstedt et al.

(10) Patent No.: US 12,310,879 B2
(45) Date of Patent: May 27, 2025

(54) EMPTYING DEVICE

(71) Applicant: OstomyCure AS, Oslo (NO)

(72) Inventors: Kristoffer Jens Olle Apelstedt, Jönköping (SE); David Karl Theodor Hvirf, Jönköping (SE); Mats Erik Kindahl Cardell, Nacka (SE)

(73) Assignee: OstomyCure AS, Oslo (NO)

( * ) Notice: Subject to any disclaimer, the term of this patent is extended or adjusted under 35 U.S.C. 154(b) by 0 days.

(21) Appl. No.: 18/858,831

(22) PCT Filed: Apr. 24, 2023

(86) PCT No.: PCT/EP2023/060655
§ 371 (c)(1),
(2) Date: Oct. 22, 2024

(87) PCT Pub. No.: WO2023/203251
PCT Pub. Date: Oct. 26, 2023

(65) Prior Publication Data
US 2025/0107919 A1  Apr. 3, 2025

(30) Foreign Application Priority Data
Apr. 22, 2022 (EP) ..................................... 22169488

(51) Int. Cl.
*A61F 5/44* (2006.01)
*A61F 5/445* (2006.01)
*A61F 5/448* (2006.01)

(52) U.S. Cl.
CPC ............ *A61F 5/4404* (2013.01); *A61F 5/445* (2013.01); *A61F 2005/4455* (2013.01); *A61F 2005/4486* (2013.01)

(58) Field of Classification Search
CPC .............. A61F 2005/4404; A61F 5/445; A61F 2005/4455; A61F 2005/4486
See application file for complete search history.

(56) References Cited

U.S. PATENT DOCUMENTS 4,183,357 A * 1/1980 Bentley ............. A61M 39/0247
604/339
4,510,621 A 4/1985 Sak et al.
(Continued)

FOREIGN PATENT DOCUMENTS

EP  0815812 A1  1/1998
EP  1557145 A2  7/2005
(Continued)

OTHER PUBLICATIONS

International Search Report & Written Opinion dated Jun. 15, 2023 pertaining to PCT International application No. PCT/EP2023/060655 filed Apr. 24, 2023, pp. 1-13.

*Primary Examiner* — Guy K Townsend
(74) *Attorney, Agent, or Firm* — DINSMORE & SHOHL LLP (57) ABSTRACT

An emptying device assembly for evacuation of a stoma includes a first film layer and a second film layer. The first film layer and second film layer are attached along a peripheral part to form an emptying device, wherein the first film layer has a first hole. An integrated connector ring includes: an annular base defining a second hole concentric with the first hole, wherein the annular base is attached, to the emptying device assembly around the first hole; and a plurality of radially inwardly protruding flanges, wherein at least a subset of the protruding flanges are adapted to engage with an outer circumferential groove of a cylindrical ostomy implant or a lid of an ostomy implant. A method of manufacturing the emptying device assembly is also disclosed.

20 Claims, 4 Drawing Sheets

(56) References Cited

U.S. PATENT DOCUMENTS

| | | | | |
|---|---|---|---|---|
| 4,930,502 A * | 6/1990 | Chen | ............... | A61B 17/11 606/150 |
| 5,139,492 A * | 8/1992 | Leise, Jr. | ............... | A61F 5/448 604/339 |
| 5,269,774 A * | 12/1993 | Gray | ............... | A61F 5/449 604/338 |
| 6,033,390 A * | 3/2000 | von Dyck | ............... | A61F 5/445 604/174 |
| 6,485,476 B1 * | 11/2002 | von Dyck | ............... | A61F 5/441 604/332 |
| 8,398,669 B2 * | 3/2013 | Kim | ............... | A61F 2/04 604/101.01 |
| 2001/0039425 A1 * | 11/2001 | Dakov | ............... | A61B 17/11 606/153 |
| 2002/0077611 A1 * | 6/2002 | von Dyck | ............... | A61F 5/442 604/332 |
| 2008/0262450 A1 * | 10/2008 | Shah | ............... | A61F 5/445 604/338 |
| 2012/0123361 A1 * | 5/2012 | Johansson | ............... | A61F 5/445 604/338 |
| 2013/0079738 A1 * | 3/2013 | Hanuka | ............... | A61F 5/445 604/335 |
| 2015/0126946 A1 * | 5/2015 | Fernandez | ............... | A61F 5/448 604/342 |
| 2016/0030227 A1 * | 2/2016 | Brönnimann | ............... | A61F 5/445 604/338 |
| 2016/0045358 A1 * | 2/2016 | Brönnimann | ............... | A61F 5/445 604/338 |
| 2016/0045359 A1 * | 2/2016 | Brönnimann | ............... | A61F 5/449 604/338 |
| 2017/0367871 A1 * | 12/2017 | Dinakara | ............... | A61F 5/445 |
| 2018/0049909 A1 * | 2/2018 | Johnson | ............... | A61F 5/445 |

FOREIGN PATENT DOCUMENTS

| | | |
|---|---|---|
| TW | 201700071 A | 1/2017 |
| WO | 2014020095 A1 | 2/2014 |

* cited by examiner

EMPTYING DEVICE

CROSS-REFERENCE TO RELATED APPLICATIONS

The present application is the National Phase entry of International Patent Application No. PCT/EP2023/060655, filed Apr. 24, 2023, which claims priority to European Patent Application No. 22169488.8, filed Apr. 22, 2022, the entire contents of both are hereby incorporated by reference into this application.

TECHNICAL FIELD

The present disclosure relates to an emptying device, in particular an emptying pouch and an emptying sleeve for evacuation of a stoma.

BACKGROUND

Ileostomy and colostomy are common operations which may be necessitated, for example, by malignancy or chronic bowel inflammation. The surgery is called an ileostomy if the colon and rectum are removed and a colostomy if the rectum alone is removed. Similarly, an abdominal urostomy is created when the urinary bladder has to be removed due to, for example, bladder cancer. In these operations, a stoma is formed in the abdominal wall to which a bowel segment is connected.

Ileostomy is a stoma constructed by bringing the end or loop of small intestine (the ileum) out onto the surface of the skin, or the surgical procedure which creates this opening. Intestinal waste passes out of the ileostomy and is collected in an external ostomy system which is placed over the opening.

A colostomy is a stoma in the large intestine (colon), or the surgical procedure that creates one. The opening is formed by drawing the healthy end of the colon through an incision in the anterior abdominal wall and suturing it into place. This opening, often in conjunction with an attached ostomy system, provides an alternative channel for feces to leave the body.

An ostomy pouching system is a medical device that provides a means for the collection of waste from a stoma. Traditional pouching systems usually consist of a collection pouch, a barrier on the skin, and connect with the stoma itself, which is the part of the body that has been diverted to the skin.

In the traditional ostomy pouching systems, the ostomy bags are typically attached directly to the skin.

As an alternative to traditional ostomy pouching systems, an implant-based system has been developed. This system is based on a percutaneous ostomy implant, which is anchored in the body of the user and allows serosal tissue of a bowel segment to attach to the implant. The ostomy implant comprises a usually cylindrical body with an open end, to which a lid may be attached. When the lid is removed, the open end can be connected to an emptying device, such as an ostomy pouch. The solution allows the users to exercise their needs when it suits them and minimizes skin complications as well as discomfort, noise and smell.

Attaching an ostomy pouch to an ostomy implant is, however, associated with several technical challenges related to, for example, ease of use, potential leakages, and the ability to withstand forces caused by waste in the ostomy pouch. A number of prior devices have attempted to address these limitations. U.S. Pat. No. 5,269,774 discloses a combination ring and collection pouch for an ostomy, said combination comprising a ring portion having a first side, a second side and an aperture substantially centered through said first side and said second side. U.S. Pat. No. 5,139,492 discloses a two-piece ostomy appliance comprising a pouch and a faceplate having matching coupling rings. US 2012/0123361 discloses a percutaneous ostomy implant for implantation into the abdominal wall of a patient. U.S. Pat. No. 4,183,357 discloses a chronic transcutaneous implant device for enterostomies comprised of a barrel portion and flange portion.

While these documents address some limitations of traditional pouch systems, there are still significant drawbacks that need to be addressed in terms of for example leakage prevention, ease of use and the prevention of accidental disconnection between the pouch system and the stoma.

SUMMARY

The present disclosure relates to an emptying device assembly for evacuation of a stoma, comprising:
  a first film layer and a second film layer, said first film layer and second film layer being attached along a peripheral part to form an emptying device, wherein the first film layer comprises a first hole; and
  an integrated connector ring comprising:
    an annular base defining a second hole that is concentric with the first hole, wherein the annular base is attached, such as welded, to the emptying device around the first hole;
    a plurality of radially inwardly protruding flanges, wherein at least a subset of the protruding flanges are adapted to engage with an outer circumferential groove of a cylindrical ostomy implant or a lid of an ostomy implant.

The connector ring can be attached to a lid of an ostomy implant. Preferably the connector ring is attached to the lid by positioning the subset of the protruding flanges to fit into the circumferential groove of the lid. From this position the emptying device, in case it is a closed pouch can be opened in one end. The lid can then be opened from the outside of the emptying device to avoid soiling the hands of the user.

Preferably, the plurality of radially inwardly protruding flanges of the connector ring comprise engagement flanges adapted to engage with an outer circumferential groove of a cylindrical ostomy implant or a lid of an ostomy implant. The engagement flanges may be made of a resilient, yet relatively rigid, material, such that the engagement can flex slightly when the connector ring is positioned, but once the connector ring is in the right position the engagement flanges will go back to their original non-flexed shape. This may cause a click sound. The engagement flanges may have hooks or guide elements at an inner engagement flange edge towards the center of the second hole. The hook or guide elements may increase the ability of the connector ring to stay in the attached position even if the emptying device contains waste from the stoma.

A further improvement for the ability to carry the weight of the emptying device is the possibility of having further radially inwardly protruding flanges comprising support flanges adapted to stabilize the integrated connector ring. The support flanges may be generally stiff and slightly shorter than the engagement flanges. The support flanges may have an inner support flange edge towards the center of the second hole, wherein the support flanges are dimensioned such that the inner support flange edges are, during use, to abut an outer circumferential ring of the cylindrical ostomy implant or the lid of the ostomy implant. The support flanges can thus contribute to the overall structural strength of the connector ring without affecting the usability. The protruding flanges may be arranged such that every second radially inwardly protruding flange is an engagement flange and every second radially inwardly protruding flange is a support flange.

The present disclosure further relates to a method of manufacturing an emptying device assembly according to any one of the preceding claims, the method comprising the steps of (in any order):
- attaching a first film layer and a second film layer along peripheral parts of the layers to form a sleeve or pouch;
- forming a first circular hole in the first film layer;
- attaching a connector ring to the first film layer around the first hole, wherein the connector ring comprises:
  - an annular base defining a second hole concentric with the first hole; and
  - a plurality of radially inwardly protruding flanges, wherein at least a subset of the protruding flanges are adapted to engage with an outer circumferential groove of a cylindrical ostomy implant or a lid of an ostomy implant.

In yet a further aspect, the present disclosure relates to a connector ring for attachment of a further device to an ostomy implant or a lid of an ostomy implant, the connector ring comprising:
- an annular base defining a connector hole; and
- a plurality of radially inwardly protruding flanges, wherein at least a subset of the protruding flanges are adapted to engage with an outer circumferential groove of a cylindrical ostomy implant or a lid of an ostomy implant.

The connector ring may comprise attachment means for attachment of the further device to the connector ring, such as adhesives, alternatively, the connector ring may form an integral part of the further device, such as wherein the connector ring has been welded to the further device, e.g. by plastic welding.

Yet a further aspect of the present disclosure relates to use of a connector ring for attachment of a further device to an ostomy implant or a lid of an ostomy implant.

DETAILED DESCRIPTION

The present disclosure relates to an emptying device assembly for evacuation of a stoma. The emptying device assembly comprises at least an emptying device and a connector ring. The emptying device advantageously comprises a first film layer and a second film layer that are attached such that a compartment is formed between the first film layer and the second film layer. The first and second film layer may for example have been formed by separate film layers or may have been formed from a single layer that has been folded to form a first film layer covering a second film layer. Alternatively, the emptying device may have been formed from a single component, typically a polymer component, for example by blow molding. Thus, the first and the second film layer may be different parts, including for example partly overlapping parts, of the same surface.

In any event, the first and second film layers are preferably attached/connected along a peripheral part such that a compartment is formed between the first and the second film layer. The compartment may be connected to the exterior environment through a number of openings/holes in, and/or between, the first and the second film layer, such as one, two, or even three holes. Thus, the attachment/connection of the first and the second film layer, may be made by aligning a first film layer and a second film layer, and attaching the two film layers along a peripheral part of said layers. For example, along at least a part of a perimeter, such as the entire perimeter. In specific examples at least one of the first and the second film layer comprise a hole, before attachment/connection of the film layers, in other examples at least one hole in either the first or the second film layer is formed subsequent to attaching said film layers.

The emptying device typically comprises a compartment, between the first and second film layers, and may further comprise one or more holes, such as a first hole.

Alternatively, the one or more holes may be formed subsequent to forming the emptying device, for example in the first film layer and/or the second film layer. In specific examples, the first and the second film layer is attached/connected only along a part of the perimeters of said film layers, such that a hole is formed at an end of the emptying device, i.e. wherein the first and the second film layer is not attached. Said hole may for example be arranged to empty content of the emptying device At least one of the film layers, such as the first film layer, advantageously comprises a first hole. Preferably, an integrated connector ring is attached/connected to the area of the first film layer surrounding said first hole, as such the connector ring may be considered an integrated part of the emptying device assembly. However, the integrated connector ring may be detachable from the first and/or second film layer, thus integrated shall not be understood as limiting the integrated connector ring to embodiments wherein the connector ring is not detachable from the emptying device (e.g. to the first and/or second film layer). Integrated, as used herein, refers to a part that is attached or connected to another part, the two parts in this example are in this way integrated into an assembly (comprised of said two parts).

The integrated connector ring preferably comprises a base defining a second hole, also known as a connector hole, that is at least partially concentric with the first hole, preferably wherein the first hole and the second hole are fully concentric. The connector ring typically forms an annulus, and as such, the second hole may be defined by the radially inner circle of said annulus. In specific examples the first hole and the second hole coincide, however in other examples the size, such as the radius, of the second hole is larger than the size, such as the radius, of the first hole.

The first hole and the second hole are preferably formed having the same shape. For example, the first and the second hole may have a circular, oval, rectangular or quadratic shape. However, preferably, the first and second holes have a circular shape. The base of the integrated connector may have an annular base, defining a second hole having a circular shape. Alternatively, the integrated connector may have any other shape as mentioned above, in order to define a second hole that has a shape different from circular. Preferably, the base is an annular base and/or the second hole has a circular shape, and/or the first hole has a circular shape. The base is preferably attached to the emptying device, preferably to the area of the first film layer surrounding the first hole. The base may for example be welded to the area surrounding the first hole, for example by thermowelding or solvent-welding. However, in other embodiments of the present disclosure, the base may be attached to the area surrounding the first hole through other means, such as through the use of adhesives.

The integrated connector ring typically comprises a plurality of flanges protruding inwardly, preferably radially inwardly. It is a further preference that said flanges, or a subset thereof, are arranged to engage with an ostomy implant and/or a lid of an ostomy implant. Said flanges may thus be referred to as engagement flanges. The flanges of the connector ring or a subset thereof, i.e. the engagement flanges, may thus be arranged to engage with an ostomy implant and/or a lid of an ostomy implant. Preferably, wherein the engagement flanges are arranged to engage with a connection means of an ostomy implant and/or a lid of an ostomy implant. The connection means of the ostomy implant and/or a lid of an ostomy implant may be one or more of a raised and/or lowered part, a ridge, a protrusion, an indentation, a groove, a hook, a recess and/or a pit, preferably wherein said connection means is circumferential, such as one or more of a raised and/or lowered circumferential part, a circumferential ridge, a circumferential protrusion, a circumferential indentation, a circumferential groove, a circumferential hook, a circumferential recess and/or a circumferential pit. Most preferably, the engagement flanges are arranged to engage with a circumferential groove of an ostomy implant and/or the lid of an ostomy implant.

It is a preference that the connector comprises restriction means, for restricting bending of the engagement flanges in a direction, and, during use, to secure the connector to the ostomy implant and/or lid. Typically, the restriction means are arranged such that the engagement flanges (e.g. at least the edge part) may be bent inwards (i.e. into the compartment formed between the first and the second film layer). During use, the engagement flanges may thus be arranged to easily engage with the connection means of the ostomy implant and/or the lid of an ostomy implant, by being bent inwards (i.e. inwards towards the compartment formed between the first and second film layer). The bending of said flanges is typically required as the diameter of the ostomy implant and/or the lid of an ostomy implant is larger than the circle/annulus formed by the inner engagement flange edges. However, said annulus/circle is preferably sized to match the connection means of the ostomy implant/lid.

At the same time, while allowing for easy engagement, the restriction means is preferably arranged to restrict the bending of each engagement flanges, or a subset thereof, in the opposite direction, i.e. in the direction away from the second film layer (i.e. outwards). This secures the connection between the connector and the ostomy implant and/or lid. Typically, the engagement flanges are arranged such that accidental disconnection between the connector and the ostomy implant and/or lid is avoided, for example even when the emptying device contains a large amount of waste and therefore has a considerable weight. At the same time, while preferably allowing for accidental disconnection, it is a preference that a person without significant force is capable of disconnecting the connector and the ostomy implant and/or lid.

Thus, the restriction means, may be arranged to restrict bending of one or more engagement flanges in a first direction but allowing bending of the engagement flanges in a direction opposite of the first direction. Typically, the restriction means restricts bending in the direction at which the restriction means are located. For example, if the restriction means are located on a first side of the connector, bending of the engagement flanges towards the first side may be restricted. At the same time, the restriction means may be arranged to allow for bending of the engagement flanges in an opposite direction (i.e. opposite to the first side).

The restriction means may comprise or consist of one or more protrusions, recesses, grooves and/or indentations, that are arranged such that the engagement flanges are more easily bent inwards (i.e. in the direction of the compartment formed between the first film layer and the second film layer) than outwards (i.e. away from the compartment formed between the first film layer and the second film layer).

In a preferred example, the restriction means comprise a radially outer protrusion and a radially inner protrusion, i.e. wherein said radially outer protrusion is located radially outwards of the radially inner protrusion (i.e. the radially outer protrusion is located further away from the center of the second hole compared to the radially inner protrusion). Preferably, the radially outer protrusion and the radially inner protrusions are arranged on the outwardly facing side of the connector (i.e. away from the compartment formed between the first and second film layer).

The radially inner protrusion is preferably adjacently arranged to the radially outer protrusion, such as when the engagement flanges are not bent, however the radially inner protrusion is preferably arranged radially inwardly (i.e. towards the center of the second hole) from the radially outer protrusion. Such an arrangement allows for bending of the engagement flanges between the outer and inner protrusions, when a user is positioning the connector to engage with the implant and/or lid.

However, the protrusions restrict bending of the engagement flanges in an opposite direction (i.e. away from the compartment formed between the first and second film layer), and thus act to secure the connector to the implant and/or lid. In these arrangements, as the protrusions are adjacent to each other, they restrict bending of the engagement flanges in a direction that is identical to the side of the connector where the protrusions are located, i.e. the outwardly facing side. The restriction means may be located entirely on one or more, such as all, of the engagement flanges, or parts of the restriction means may be located on the annular base of the connector ring. For example, the restriction means may comprise radially outer protrusions located on said base, wherein each of said protrusions are positioned adjacent to a radially inner protrusion located on the engagement flange(s). Alternatively, both protrusion may be located on the engagement flange(s).

Preferably, the emptying device assembly is arranged such that, following attachment of the emptying device assembly to a lid of an ostomy implant, at least a part of the lid protrudes into the compartment of the emptying device formed between the first and the second film layer. More preferably, the lid and preferably at least a part of the ostomy implant protrudes into said compartment following said attachment.

The emptying device may have a single opening, typically a first hole formed in the first film layer. The first hole is typically formed towards a proximal end of the emptying device. The emptying device may, as such, be an emptying pouch. In this arrangement, the emptying device assembly is arranged to maintain ostomy waste expelled into the emptying device (e.g. an emptying bag). Such an emptying device assembly is typically used wherein there is a need to evacuate the stomal waste for a prolonged period.

Preferably, if the emptying device only has a single hole, i.e. the first hole, the emptying device is equipped with tearing means for forming an emptying hole towards a distal end of the emptying device. The tearing means may for example be one or more notches, one or more perforations, and/or one or more tearing tabs, such as welded to the first and/or second film layer. Preferably, the emptying device further comprises means for resealing the emptying hole, after formation, such as velcro straps or adhesive patches. Similar tearing means for forming an emptying hole, and resealing means, may be provided for emptying devices that comprises multiple holes.

The emptying device may alternatively comprise multiple holes, such as two holes. In this embodiment, the emptying device may comprise a first hole for receiving stomal waste, typically formed in the first film layer towards a proximal end of the emptying device, and further an emptying hole for emptying of stomal waste formed at, or towards, a proximal end of the emptying device. The emptying hole may for example be formed along an edge where the first film layer is not attached to the second film layer.

Typically the first hole is formed towards a proximal end of the emptying device, while the emptying hole is formed towards a distal end of the emptying device. In this arrangement, the emptying device may be referred to as a sleeve. Preferably, the emptying device comprises means for resealing the emptying hole, such as velcro straps or adhesive patches.

The emptying device assembly may thus be arranged such that a user may wear the assembly for a prolonged time, while the user is capable of carrying out normal daily activities. During such use, it is important that the connector ring is capable of providing a secure and stable attachment to the ostomy implant and/or the lid of an ostomy implant.

Typically, a lid attached to an open end of an ostomy implant is used to seal a stoma. The emptying device and/or the emptying device assembly may be arranged to receive at least a part of the lid within the compartment formed between the first and the second film layer, through the first hole. In this position, the lid may be opened through the emptying device, i.e. through one of the first and the second film layers, in order to avoid soiling the hands of the user. The lid of the ostomy implant is typically opened by radially sliding an opening part that, in closed position, covers an opening of the lid. Thus it is a preference that the emptying device is arranged such that the user may carry out such a movement from outside of the emptying bag, i.e. through the first and/or second film layer.

Additionally, the integrated connector of the presently disclosed device allows for a secure attachment to be formed between the emptying device assembly and the lid of the ostomy implant and/or the ostomy implant. The connector ring further decreases the risk of leakages by acting to form a seal between the compartment of the emptying device and the ostomy implant and/or the lid of an ostomy implant.

Various lids for ostomy implants are known from the prior art. However, it is a strong preference that the lid comprises a connection means for engaging with the connector ring, such as the engagement flanges. Typically the connection means of the lid is provided on a base part of the lid. Further, the base is preferably arranged to seal an open end of the ostomy implant, and comprising an opening part that is adapted to move between an open position, for evacuation of waste, and a closed position, for preventing leakages of waste from the stoma. Preferably, the opening part is attached to the base both in the closed position and the open position. The opening part may for example be opened by sliding, pulling, twisting or screwing a part of the lid, in order to open the lid, preferably, by radially sliding the opening part.

Preferably, the lid is arranged such that the reverse movement of the opening part moves the lid into its closed position. Once evacuation of the stoma is complete, the user may close the lid, typically by reversing the movement of the opening part for opening of the lid. After the lid is closed, the emptying device (i.e. the emptying device assembly) may be detached from the lid, and disposed of.

Preferably, the connector ring is arranged to be attached to an ostomy implant or a lid of an ostomy implant by positioning the connector ring such that the protruding flanges, or subset thereof, preferably the engagement flanges, engage with a complementary surface of the lid and/or the ostomy implant, e.g. wherein said complementary surface is a circumferential groove of the lid and/or the ostomy implant and/or wherein said complementary surface is complementary to an inner engagement flange edge of the engagement flanges.

Alternatively or additionally, the complementary surface of the ostomy implant and/or the lid of an ostomy implant may be one or more of a raised and/or lowered part, a ridge, a protrusion, a recess, an indentation, a groove, a hook and/or a pit. Preferably, the complementary surface of the lid and/or ostomy implant is arranged such that the protruding flanges, or subset thereof, may engage with the lid and/or ostomy implant. Typically, the complementary surface is one or more of a raised and/or lowered part, a ridge, a protrusion, a recess, an indentation, a groove, a hook, and/or a pit of the lid and/or the ostomy implant that is/are complementary to an inner part (i.e. a radially inward part) of the protruding flanges, or a subset thereof, such as the engagement flanges. Typically, the complementary surface of the ostomy implant and/or the lid for an ostomy implant is a circumferential complementary surface, such as a circumferential groove.

It is a preference that the plurality of radially inwardly protruding flanges of the connector ring comprises, or consists of, engagement flanges adapted to engage with one or more of a raised and/or lowered part, a ridge, a protrusion, a recess, an indentation, a groove, a hook and/or a pit of an ostomy implant and/or a lid for an ostomy implant. Typically, the plurality of radially inwardly protruding flanges of the connector ring comprises, or consists of, engagement flanges adapted to engage with one or more circumferential raised or lowered parts, a circumferential ridge, a circumferential protrusion and/or a circumferential groove of an ostomy implant and/or a lid for an ostomy implant.

The engagement flanges may be made of a resilient, yet relatively rigid, material, such that the engagement flanges can flex slightly during attachment of the emptying device (i.e. the emptying device assembly) to the lid of the ostomy implant and/or to the ostomy implant, but once the connector is in the correct position the engagement flanges will go back to their original non-flexed shape. As such, the engagement flanges may form, together with one or more complementary surfaces on the ostomy implant or the lid for an ostomy implant, a snap fit connection/joint, such as an annular snap fit connection/joint. This allows for a reversible, yet strong, attachment between the emptying device and the lid and/or implant. Various types of snap-fit connections are known to the skilled person, including various types of complementary surfaces for forming a strong yet reversible attachment.

Typically, attachment of the connector to the lid/implant causes initially the engagement flanges to flex slightly, typically due to the slightly larger diameter of the ostomy implant and/or lid of an ostomy implant. When the engagement flanges are moved into a position where they may engage with the connection means, for example a complementary surface and/or a circumferential groove, the engagement flanges may move from the flexed position into a non-flexed position. The engagement flanges may snap into the non-flexed position, which may cause an audible click. Typically, when engaged with the lid/ostomy implant the inner engagement flange edges are in direct contact with the complementary surface.

The engagement flanges may comprise engaging means at the inner engagement flange edge, i.e. at the protruding end of the engagement flanges. The engaging means may for example comprise one or more of a raised and/or lowered part, a ridge, a protrusion, a recess, an indentation, a groove, a hook, a pit and/or a guide element that is arranged to form a connection to a complementary surface of an ostomy implant and/or a lid for an ostomy implant, e.g. a complementary surface of the connection means.

Typically, the engaging means of the connector comprise a surface that is complementary to the surface of the connection means of the ostomy implant and/or the lid for an ostomy implant. Typically the engaging means is formed along the inner engagement flange edge. As such, each engagement flange may comprise a guide element along its inner engagement flange edge, preferably wherein said guide element is complementary to a circumferential groove of an ostomy implant and/or a lid of an ostomy implant.

The engaging means of the engagement flanges provides support and stability to the attachment of the connector ring to the ostomy implant/lid and, as such, it allows for the formation of a secure connection between the emptying device assembly and the ostomy implant/lid, even in the case where the emptying bag is arranged to contain the stomal waste, which may exert a significant force on the connector ring. The presently disclosed embodiment thus offers means for a secure attachment, while simultaneously allowing for easy attachment and removal of the connector ring to the ostomy implant/lid. The effect is even more pronounced if the engagement flanges comprises engaging means, further acting to increase the support and stability offered to the connection.

A further improvement for the ability to carry the weight of the emptying device is the possibility of having further radially inwardly protruding flanges comprising support flanges adapted to stabilize the integrated connector ring, such as during use, e.g. when the connector ring is connected to a lid and/or an ostomy implant.

As such, the connector may comprise a plurality of flanges, wherein said plurality of flanges comprises or consists of a subset of engagement flanges and/or a subset of support flanges. Preferably, the connector ring comprises engagement flanges and support flanges, more preferably the connector ring comprises a plurality of radially inwardly protruding flanges wherein every second flange is a support flange and every second flange is an engagement flange, i.e. each support flange is located between two engagement flanges and vice versa.

The support flanges may be generally stiff and preferably also slightly shorter than the engagement flanges. The support flanges may have an inner support flange edge towards the center of the second hole. Preferably, the support flange is arranged such that the inner support flange edge is to abut an outer surface of an ostomy implant/lid, when engaged with said ostomy implant/lid. The outer surface may for example be an outer circumferential ring of an ostomy implant and/or of a lid of the ostomy implant. Typically the outer surface is a cylindrical surface. In this way, the support flanges are arranged to provide support to the connector ring and act to secure the connection to the ostomy implant/lid.

Advantageously, the engagement flanges and the support flanges are arranged to engage separate surfaces of the ostomy implant and/or the lid for an ostomy implant. This may for example be realized by providing the engagement flanges and the support flanges in separate planes. Alternatively, the engagement flanges may be provided with an inner engagement flange edge comprising a protrusion that is arranged to engage a corresponding recess of an ostomy implant and/or a lid of an ostomy implant, while the support flanges are provided with an inner support flange edge arranged to abut an outer surface of the ostomy implant/lid. Typically, the support flanges are arranged to abut an outer surface, such as an outer circumferential ring, that is in the vicinity of, such as next to, the complementary surface of the ostomy implant/lid, e.g. the circumferential recess.

The support flanges are typically arranged to abut a surface that is separate from the surface that the engagement flanges are arranged to engage, for example by being provided in separate planes of the connection ring. As such, the relative length of the support flanges and the engagement flanges may be of lesser importance, and instead what may be of greater importance is that the size of the annulus formed by the inner engagement flange edges matches that of the surface of the lid/ostomy implant that they are to engage e.g. the circumferential recess. Similarly, it may be of greater importance that the size of the annulus formed by the inner support flange edge matches that of the surface of the lid/ostomy implant that they are to abut, e.g. the outer circumferential ring. Thus, the inner support flange edges may form an annulus that is smaller, larger or of the same size as the annulus formed by the inner engagement flange edges.

It is a preference that the connector is attached to an outer surface of the first film layer, i.e. the surface of the first film layer that faces away from the second film layer. It is a further preference that the emptying device assembly comprises an annular protection area, for forming a protective layer around an ostomy implant or a lid for an ostomy implant. The protective layer may, during use, protect and/or provide a seal for safe evacuation of a stoma. The annular protection area may thus be arranged to, during use, contact an outer part of an ostomy implant and/or a lid of an ostomy implant. The outer part is typically a circumferential surface that is, during use, located towards the second film layer, with respect to a connection means of the implant or lid. The outer surface may for example be a circumferential surface between the connection means (i.e. the outer surface of the implant or lid) and a top part of the implant or lid, i.e. wherein the top part is located away from the user during use.

The annular protection area is thereby typically concentric with the first hole and/or the connector ring. Preferably, the annular protection area extends radially inwards from the connector ring and/or the annular attachment area of the first film layer, to which the connector ring is attached. The annular protection area may form a part of the first film layer, and in such a case the size of the first hole may be defined by the inner edge of the annular protection area. Thus, the annular protection area may be defined as the annulus between the outer part of the first hole (i.e. its circumference) and the outer part of the second hole (i.e. its perimeter). Alternatively, the annular protection area may not form part of the first film layer. Thus, in such an arrangement, the annular protection area may be a separate layer attached to the connector ring, and may at least partially overlap with the first hole.

Preferably, the annular protection area extends radially inwards from the connector ring, preferably across at least a part of the length of the flanges, more preferably across the entire length of the flanges, yet more preferably beyond the entire length of the flanges. Thus, it is a preference that the annular protection area extend radially inwards, such that is covers at least a part of the flanges, more preferably wherein the annular protection area extend radially inwards, beyond the flanges, such as at least 5 mm beyond the edge of the flanges. The annular protection area may be provided in the same plane as the connector, or in separate plane, such as in a plane between the connector ring and the first film layer, in the layer of the first film layer, or in a layer between the first film layer and the second film layer. Further, the emptying device, and/or the emptying device assembly, may comprise multiple annular protection areas for an even further improved protection and/or seal.

Preferably, the annular protection area is formed in an elastic material, preferably a plastic. In specific examples, the annular protection area does not constitute a part of the connector ring, the first film layer and/or the second film layer, although it may be connected thereto. Alternatively, the annular protection area may form part of the first film layer. In this example, the first hole in the first film layer is preferably smaller than the second hole of the connector ring. Preferably, the first hole is smaller than the annulus formed by any of the flanges, e.g. the support flanges and/or the engagement flanges. In this example, and with the connector ring concentric with the first hole, the first film may form an annular protection area that protrudes beyond said flanges. During use, the annular protection area is arranged to contact the ostomy implant/lid, preferably the annular protection area is made of an elastic material and the diameter of its inner edge is smaller than the diameter of the ostomy implant/lid, such that a seal may be formed upon attachment of the emptying device assembly to the ostomy implant/lid. It is a preference that the first film layer is made of an elastic material, preferably a plastic, thus allowing the first film layer to form the annular protection area for protecting/sealing the implant and/or lid.

For embodiments wherein the first and the second film layers are attached along their entire perimeters, such that a pouch is formed, tearing means are preferably provided at a distal end of the emptying device. This allows a user to connect the emptying device to an ostomy implant or a lid of an ostomy implant and initiate evacuation of the stoma. As known to a skilled person, under certain conditions evacuation of a stoma may be time consuming. Providing the emptying device in the form of a pouch allows the user to carry out normal daily activities while evacuating the stoma. Once the evacuation is complete, the user may dispose of the waste by positioning the distal end of the emptying device into for example a toilet, and form an opening at the distal end of the emptying device e.g. by tearing, such that the waste is expelled into the toilet.

The tearing means may consist or comprise of one or more perforations and/or tearing notches formed in the surface where the first film layer is attached to the second film layer. For example the tearing means may comprise a pair of notches located on opposite sides of a distal end of the emptying device. Alternatively, or additionally, the tearing means may comprise a tab that is attached, such as welded, to the first and/or second film layer, and wherein the tab is arranged such that pulling the tab tears an opening at the distal end of the emptying device.

Advantageously, the emptying device is arranged such that the integrated connector ring, when attached to an ostomy implant and/or a lid of an ostomy implant, forms a fluid connection between the emptying device and the stoma. Stomal waste may thereby be securely expelled from the stoma into the emptying device.

Preferably, the annular base is attached, such as welded, to the first film layer at an annular attachment area. The annular attachment area is preferably concentric with the first hole. As such, the annular attachment area may be an annular surface surrounding the first hole, and which is concentric with the first hole, i.e. the center of the annular attachment is concentric with the first hole.

In an embodiment of the present disclosure, the first film layer comprises an annular protection area extending radially inward from the annular attachment area. Preferably, the flanges, or part of the flanges, such as the support flanges and/or the engagement flanges, does not radially extend inward beyond the annual protection area. As such, the annulus formed by the inner support flange edges and/or the inner engagement flange edges are larger than the circular opening of the annular protection area, e.g. the first hole.

In an embodiment of the present disclosure, the annular protection area at least partially overlaps the first hole. The annular protection area may thus extend radially inward into at least a part of the first hole. As such, the annular protection area may be formed from a separate film layer to the first film layer. Preferably the annular protection area is concentric with the first hole, i.e. the centers of the annular protection area and the first hole coincide.

In an embodiment of the present disclosure, the first hole and the second hole are substantially circular. Further, it is a preference that the first hole and the second hole substantially overlap. As such, the center of the circular first hole may coincide with the center of the circular second hole.

In an embodiment of the present disclosure, the plurality of radially inwardly protruding flanges are separated by gaps, typically of the same size. The gaps may thus separate the support flanges from the engagement flanges and/or other support flanges, and similarly they may separate the engagement flanges from the support flanges or other engagement flanges. The gaps may enable the flanges to be moved, such as bent, independently of the neighboring flanges. Thus, the gap may facilitate individual bending of engagement flanges during attachment to an ostomy implant and/or a lid of an ostomy implant.

In an embodiment of the present disclosure, the plurality of radially inwardly protruding flanges comprise engagement flanges adapted to engage with connection means of a cylindrical ostomy implant or a lid of an ostomy implant. The connection means of the ostomy implants and/or the lid may for example comprise one or more of a raised and/or lowered part, a ridge, a protrusion, a recess, an indentation, a groove, a hook and/or a pit, preferably wherein said connection means is circumferential, such as one or more of a circumferential hook, a circumferential protrusion, a circumferential ridge, a circumferential indentation, a circumferential pit and/or a circumferential recess. Thus, the plurality of radially inwardly protruding flanges may each be adapted to engage with one or more of a raised and/or lowered part, a ridge, a protrusion, a recess, an indentation, a groove, a hook and/or a pit, preferably wherein said connection means is circumferential, such as one or more of a circumferential hook, a circumferential protrusion, a circumferential ridge, a circumferential indentation, a circumferential pit and/or a circumferential recess.

In a specific example, the connection means is an outer circumferential groove of a cylindrical ostomy implant and/or a lid of an ostomy implant. The engagement flanges are thus each adapted to engage said circumferential groove, for example by each comprising an inner engagement flange edge adapted to engage with said groove, for example wherein said inner engagement flange edge comprises a surface that is complementary to said circumferential groove, preferably wherein said inner engagement flange edge comprises a guide element.

In a preferred embodiment of the present disclosure, each engagement flange has a hook element or a guide element at an inner engagement flange edge towards the center of the second hole. Preferably, the hook element or guide element is dimensioned to fit into the circumferential groove of the cylindrical ostomy implant or the lid of the ostomy implant.

Preferably, each engagement flange may have one or more of a raised and/or lowered part, a ridge, a protrusion, a recess, an indentation, a groove, a hook element, a pit and/or a guide element, preferably formed along at least a part of the inner engagement flange edge of each engagement flange.

In an embodiment of the present disclosure, the engagement flanges are made of a resilient material. It is a preference that the engagement flanges are resilient and/or flexible, as the annulus formed by the inner engagement flange edges are typically smaller than the diameter of the part of the ostomy implant and/or the lid of an ostomy implant that said flanges need to be moved across during attachment. Typically, when the engagement flanges engage with the ostomy implant and/or the lid of an ostomy implant, the engagement flanges snaps back into their original unbent configuration, typically with an audible click. At this position, the engagement flanges typically engage with a complementary surface, such as a complementary circumferential surface, of the ostomy implant and/or the lid of an ostomy implant. In order to reach said complementary surface, the engagement flanges typically have to be slightly bent, i.e. when the ostomy implant and/or the lid of an ostomy implant passes through the connector ring. As such, the engagement flanges may be arranged to engage the ostomy implant and/or the lid of an ostomy implant through a snap-fit mechanism.

In an embodiment of the present disclosure, the plurality of radially inwardly protruding flanges comprise support flanges adapted to stabilize the integrated connector ring. Preferably, the support flanges are generally stiff. The support flanges are thus preferably stiffer than the engagement flanges.

It is a further preference that each support flange has an inner support flange edge towards the center of the second hole, wherein the support flange is dimensioned such that the inner support flange edge abuts an outer circumferential ring of the cylindrical ostomy implant or the lid of the ostomy implant. The support flange may be positioned in the same plane as the engagement flanges, or alternatively, they may be positioned in a plane separate to the plane of the engagement flanges. By the provision of support flanges and engagement flanges in separate planes, the support offered by the connector ring, for attachment of the emptying device assembly, may be increased.

It is a further preference that each support flange has a support structure. The support structure provides increased support to the overall structure. The support structure may thus allow for increased rigidity of the connector ring, both when the connector ring is attached/connected to a lid for an ostomy implant or to an ostomy implant, as well as when the connector ring is not attached to said lid and ostomy implant. The support structure may thus increase the structural rigidity, for example the flexural rigidity or the bending stiffness of the connector ring.

The support structure typically comprises at least one radially extending support element and/or at least one edge support element disposed along the inner support flange edge.

It is a preference that every second radially inwardly protruding flange is an engagement flange and every second radially inwardly protruding flange is a support flange. Thus, each support flange may neighbor two engagement flanges, and each engagement flange may neighbor two support flanges. This arrangement of the flanges has been shown to increase the structural rigidity of the connector, and thus of the ability to provide a secure means for attachment of an emptying device assembly to an ostomy implant and/or to a lid for an ostomy implant.

In a preferred embodiment of the present disclosure, the engagement flanges protrude more than the support flanges. As such, the engagement flanges may protrude radially inwardly more than the support flanges. The annulus formed by the inner engagement flange edges may thus be smaller than the annulus formed by the inner support flange edges. However, as specified elsewhere herein, this arrangement may depend on the structure of the ostomy implant and/or the lid of an ostomy implant to which the emptying device assembly is to be attached to, and/or whether the different types of flanges are to be located in the same plane or separate planes.

In an embodiment of the present disclosure, the support flanges are stiffer than the engagement flanges. The stiffness may be attributed by the material and/or the dimension of the flanges. However, the support flanges are preferably stiffer than the engagement flanges. In this way, the engagement flanges may be arranged to easily engage with the ostomy implant and/or the lid for an ostomy implant, e.g. by bending and snapping into position, while the short and more rigid support flanges abut an outer surface of the ostomy implant and/or the lid for an ostomy implant. It has been shown that this arrangement of flanges provides for safe attachment of the emptying device assembly to the ostomy implant and/or the lid for an ostomy implant, even in the case where the emptying device is a pouch and the connection has to be able to withstand the weight of the waste collected in the pouch.

In an embodiment of the present disclosure, the emptying device has a tapered shape, preferably a substantially flat, tapered shape. In an embodiment of the present disclosure, the emptying device has a shape of a triangle with one truncated corner.

In an embodiment of the present disclosure, the emptying device is an open-ended emptying sleeve.

In an embodiment of the present disclosure, the emptying device is an emptying pouch. Preferably, the emptying pouch comprises a tearing means, such as one or more tabs, perforations and/or notches for opening of one end of the emptying pouch.

A further aspect of the present disclosure relates to a method of manufacturing an emptying device and/or an emptying device assembly as disclosed herein. The method comprises attaching a first film layer and a second film layer along peripheral parts of the layers, thereby forming a sleeve or a pouch having a compartment between the first and second film layer. As such, the first and second film layer may be attached along their entire perimeter, thus forming a pouch. In other examples the first and second film layers are attached along only a part of their perimeters, such that an opening is formed along the non-attached part of the perimeters.

The method preferably comprises forming a first circular hole in the first film layer, or alternatively the first film layer may be provided with a first circular hole, thus the first circular hole may be present before attaching the first film layer and the second film layer.

The method preferably comprises attaching a connector ring to an annular attachment area of the first film layer, wherein the annular attachment is arranged around the first hole. The connector is typically attached to the outer side of the first film layer, i.e. the side of the first film layer that is facing away from the second film layer. The annular base of the connector ring is typically attached to the first film layer such that its center coincides with the center of the first hole. The annular base may define a second hole concentric with the first hole. However, preferably the centers of the first hole and the second holes coincide. For example, the first hole may be smaller than, and concentric with, the second hole.

The integrated connector ring typically comprises a plurality of flanges protruding inwardly, preferably radially inwardly. It is a further preference that said flanges, or a subset thereof, are arranged to engage with an ostomy implant and/or a lid of an ostomy implant. Said flanges may thus be referred to as engagement flanges. The flanges of the connector ring or a subset thereof, i.e. the engagement flanges, may thus be arranged to engage with an ostomy implant and/or a lid of an ostomy implant. Preferably, wherein the engagement flanges are arranged to engage with a connection means of an ostomy implant and/or a lid of an ostomy implant. The connection means of the ostomy implant and/or a lid of an ostomy implant may be one or more of a raised and/or lowered part, a ridge, a protrusion, an indentation, a groove, a hook, a recess and/or a pit, preferably wherein said connection means is circumferential, such as one or more of a raised and/or lowered circumferential part, a circumferential ridge, a circumferential protrusion, a circumferential indentation, a circumferential groove, a circumferential hook, a circumferential recess and/or a circumferential pit.

Most preferably, the engagement flanges are arranged to engage with a circumferential groove of an ostomy implant and/or the lid of an ostomy implant.

It should be noted that the order of said method is not of importance, since the first hole may be formed in the film layer before or after attachment of the first and second film layers. Similarly, the connector ring may be attached to the first film layer before formation of the first hole and/or before attachment of the first film layer to the second film layer.

As examples, the order of the steps may for example be: 1. attaching a first film layer and a second film layer along peripheral parts of the layers to form a sleeve or pouch; 2. forming a first circular hole in the first film layer; and 3. attaching a connector ring to the first film layer around the first hole. Alternatively, the order may be: 1. attaching a first film layer and a second film layer along peripheral parts of the layers to form a sleeve or pouch; 2. attaching a connector ring to the first film layer around a position of a first hole; and 3. forming a first circular hole in the first film layer. Alternatively, the order may be: 1. forming a first circular hole in a first film layer; 2. attaching the first film layer and a second film layer along peripheral parts of the layers to form a sleeve or pouch; and 3. attaching a connector ring to the first film layer around the first hole. Alternatively, the order may be: 1. forming a first circular hole in a first film layer; 2. attaching a connector ring to the first film layer around the first hole; and 3. attaching the first film layer and a second film layer along peripheral parts of the layers to form a sleeve or pouch. Alternatively, the order may be: 1. attaching a connector ring to the first film layer around a position of a first hole; 2. forming a first circular hole in a first film layer; and 3. attaching the first film layer and a second film layer along peripheral parts of the layers to form a sleeve or pouch. Alternatively, the order may be 1. attaching a connector ring to the first film layer around a position of a first hole; 2. attaching the first film layer and a second film layer along peripheral parts of the layers to form a sleeve or pouch; and 3. forming the first circular hole in a first film layer, at the position of the first hole.

A further improvement for the ability to carry the weight of the emptying device is the possibility of having further radially inwardly protruding flanges comprising support flanges adapted to stabilize the integrated connector ring. As such, the connector may comprise a plurality of flanges, wherein said plurality of flanges comprises or consists of a subset of engagement flanges and/or support flanges. Preferably, the connector comprises engagement flanges and support flanges, more preferably wherein every second flange is a support flange and every other second flange is an engagement flange.

The support flanges may be generally stiff, typically stiffer than the engagement flanges. Further, the support flanges may be slightly shorter than the engagement flanges. The support flanges may have an inner support flange edge towards the center of the second hole, wherein the support flange is dimensioned such that the inner support flange edge abuts an outer circumferential ring of the cylindrical ostomy implant and/or the lid of the ostomy implant. The support flanges can thus contribute to the overall structural strength of the connector ring without affecting the usability. The protruding flanges may be arranged such that every second radially inwardly protruding flange is an engagement flange and every second radially inwardly protruding flange is a support flange. The support flanges and the engagement flanges may be located in different planes for increased support. The support flanges may as such be arranged to prevent axial tilting of the connector ring when attached to an ostomy implant and/or the lid for an ostomy implant.

It is a preference that the connector is positioned on the outer surface of the first film layer, i.e. away from the compartment formed between the two inner surfaces of the first film layer and the second film layer. The connector is thus exposed and capable of being connected to an ostomy implant or a lid for an ostomy implant.

It is a further preference that the connector comprises an annular protection area, for forming a protective layer around an ostomy implant or a lid for an ostomy implant. The protective layer may, during use, protect and/or provide a seal for safe evacuation of a stoma. The annular protection area may thus be arranged to contact an outer surface of an ostomy implant or a lid of an ostomy implant.

The annular protection area is typically concentric with the first hole and/or the connector ring. Preferably, the annular protection area extends radially inwards from the connector ring, or the area of the first film where the connector ring is attached. Thus, the size of the first hole may be defined by the annular protection area.

Preferably, the annular protection area extends radially inwards beyond the flanges, i.e. the support flanges and/or the engagement flanges. The annular protection area may be provided in the same planar layer as the connector, or in a layer below the connector ring, such as between the connector ring and the first film layer, in the layer of the first film layer, or in a layer between the first film layer and the second film layer.

Preferably, the annular protection area is formed in an elastic material, preferably a plastic. The annular protection area may be formed by a separate material from, although potentially connected to, the connector ring, the first film layer and/or the second film layer. However, the annular protection area may also be formed by the first film layer. In this example, the hole in the first film layer is made smaller than the annulus formed by any of the flanges, e.g. the support flanges and/or the engagement flanges. With the connector ring being concentric with the first hole, the first film layer thus protrudes beyond said flanges and thereby forms an annular protection area for connecting, during use, to an ostomy implant or a lid for an ostomy implant. Thus in an embodiment of the present disclosure the first hole is formed having a size, e.g. diameter, that is smaller than the annulus formed by any of the flanges of the connector, such as the engagement flanges and/or the support flanges.

For embodiments wherein the first and the second film layers are attached along their entire perimeters, such that a pouch is formed, tearing means are preferably provided at a distal end of the emptying device. This allows a user to connect the emptying device to an ostomy implant or a lid of an ostomy implant and initiate evacuation of the stoma. As known to a skilled person, under certain conditions evacuation of a stoma may be time consuming. Providing the emptying device in the form of a pouch allows the user to carry out normal daily activities while evacuating the stoma. Once the evacuation is complete, the user may position the distal end of the emptying device into for example a toilet, and tear an opening at the distal end of the emptying device such that the emptying device is emptied.

The tearing means may comprise or consist of one or more perforations or tearing notches formed in the surface where the first film layer is attached to the second film layer. For example the tearing means may comprise a pair of notches located on opposite sides of a distal end of the emptying device. Alternatively, or additionally, the tearing means may comprise a tab that is attached, such as welded, to the first and/or second film layer, and wherein the tab is arranged such that pulling the tab tears an opening at the distal end of the emptying device.

In a further aspect, the present disclosure relates to a connector ring for attachment of a further device to an ostomy implant or a lid of an ostomy implant, the connector ring comprising:
  an annular base defining a connector hole; and
  a plurality of radially inwardly protruding flanges, wherein at least a subset of the protruding flanges are adapted to engage with an outer circumferential groove of a cylindrical ostomy implant or a lid of an ostomy implant.

Preferably, the connector ring is as disclosed elsewhere herein. The connector ring may for example be arranged to facilitate connection between an emptying device (such as be connected to an ostomy bag, a catheter or a sleeve) and an ostomy implant and/or a lid.

DETAILED DESCRIPTION OF THE DRAWINGS

The invention will in the following be described in greater detail with reference to the accompanying drawings. The drawings are exemplary and are intended to illustrate some of the features of the presently disclosed emptying device assembly and the method of manufacturing an emptying device according to the present disclosure, and are not to be construed as limiting to the presently disclosed invention.

Figure 1:
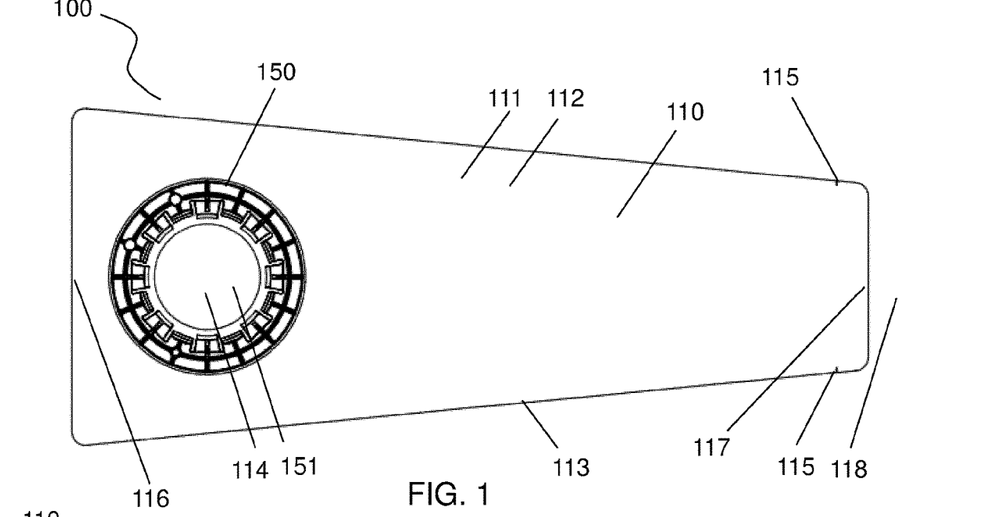
FIG. 1 shows an embodiment of the presently disclosed emptying device assembly for evacuation of a stoma.

FIG. 1 shows a top-down view of an embodiment of the presently disclosed emptying device assembly (100) for evacuation of a stoma. The emptying device assembly (100) for evacuation of a stoma can be seen to comprise an emptying device (110) comprising a first film layer (111) and a second film layer (112), wherein said first film layer and second film layer being attached along a peripheral part (113) to form the emptying device (110). The exemplified emptying device (110) is a pouch, however as disclosed elsewhere herein the emptying device (111) could for example be open-ended emptying sleeve, for example if the first and the second film layer is not attached along a distal end (117) of the emptying device (111). Typically the emptying device has a tapered shape, such as a tapered conical shape. The emptying device is preferably tapered from the proximal end (116) towards the distal end (117). As such, the emptying device (110) may be referred to as having a triangular shape with a truncated corner (118). Thus, the length of the distal end (117) is typically shorter than the length of the proximal end (116).

The emptying device assembly further comprises a first hole (114), formed in the first film layer of the emptying device. The first hole is typically formed towards a proximal end (116) of the emptying device. The emptying device comprises tearing means (115), here shown as a pair of notches formed towards the distal end (117) of the emptying device. Preferably, the notches, or any other form of tearing means, is provided in the surface wherein the first film layer is attached to the second film layer.

The emptying device assembly further comprises an integrated connector ring (150) arranged around the first hole (114). The connector ring is attached to the outer surface of the first film layer (111). The connector ring comprises an annular base that defines a second hole (151), also known as a connector hole, and wherein the second hole is concentric with the first hole, i.e. the centers of the first and second holes coincide. The annular base of the connector ring is attached, such as welded, to the emptying device around the first hole.

Figure 2:
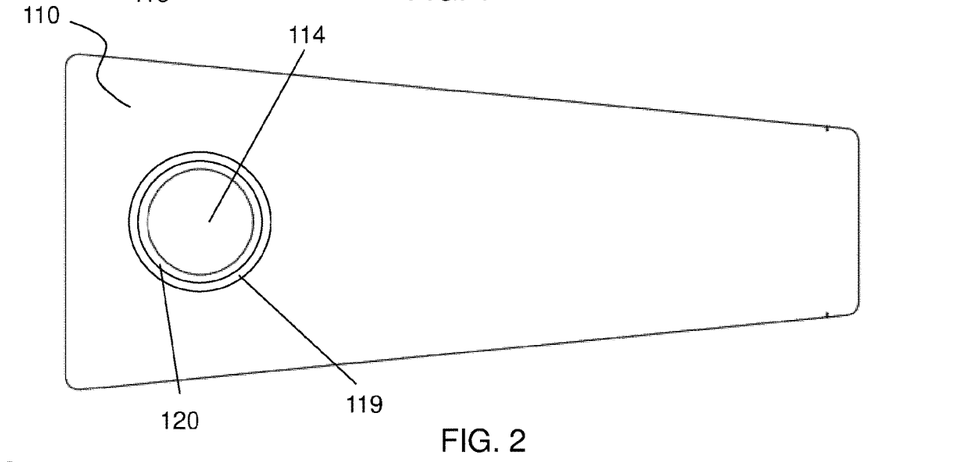
FIG. 2 shows an upper view of an embodiment of an emptying device.

The emptying device (110) of the emptying device assembly (100) is shown in FIG. 2. It can be seen that the emptying device comprises an annular attachment area (119) and an annular protection area (120) surrounding the first hole (114). It can be considered that the size of the annular protection area defines the size, i.e. diameter, of the first hole. The connector ring (150) is attached to the annular attachment area (119) such that the centers of the second hole (151) and the first hole (114) coincide, and wherein the first hole (114) is smaller than the second hole (151), as can be seen in FIG. 1.

Figure 3:
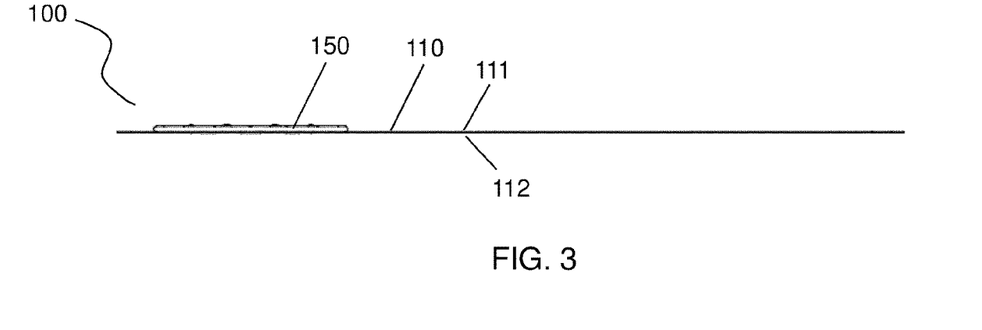
FIG. 3 shows a side view of an embodiment of an emptying device assembly.

FIG. 3 shows a side-view of the emptying device assembly (100). The emptying device (110) can be seen to comprise a first film layer (111) that is attached and overlaps with the second film layer (112). Further, the connector ring (150) is provided towards a proximal end (116) of the emptying device (110), and attached to the first film layer (111).

Figure 4:
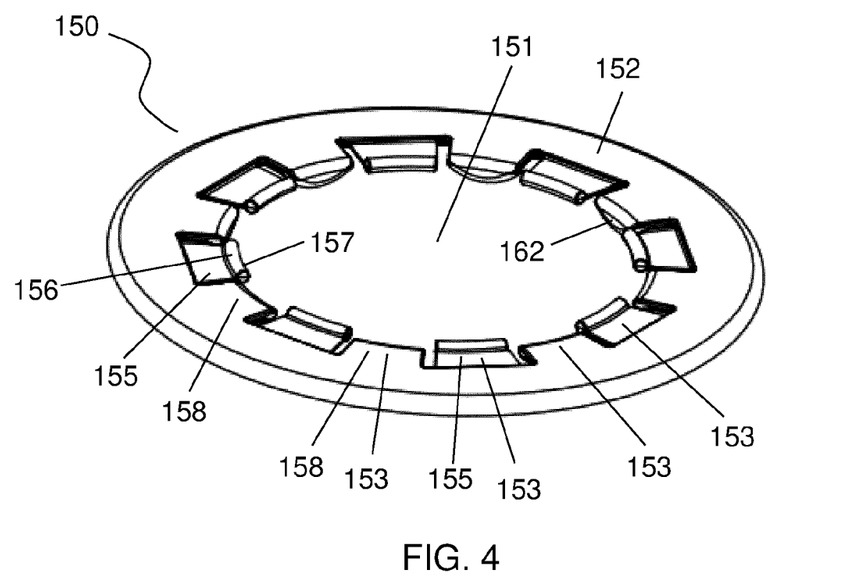
FIG. 4 shows a perspective view of an embodiment of a connector ring.

FIG. 4 shows a perspective view of the connector ring (150) comprising an annular base (152) defining a second hole (151), also known as a connector hole, that is concentric with the first hole. The connector ring comprise a plurality of radially inwardly protruding flanges (153), wherein at least a subset of the protruding flanges are engagement flanges (155) adapted to engage with an outer circumferential groove of a cylindrical ostomy implant (300) or a lid of an ostomy implant (200). Each engagement flange (155) has a connection means, such as a hook element/guide element (156) for engaging with a cylindrical ostomy implant (300) or a lid of an ostomy implant (200). The connection means, such as the hook element or guide element is dimensioned to fit into a circumferential groove of a cylindrical ostomy implant or a lid of the ostomy implant.

The connection means are provided at each inner engagement flange edge (157) towards the center of the second hole (151). The connector ring further comprises support flanges (158) protruding radially inwards. The inner engagement flange edges (157) form a circle/annulus that is smaller than that formed by the inner support flange edges (160). Thus, the engagement flanges (155) protrude further radially inward than the support flanges (158).

Figure 5:
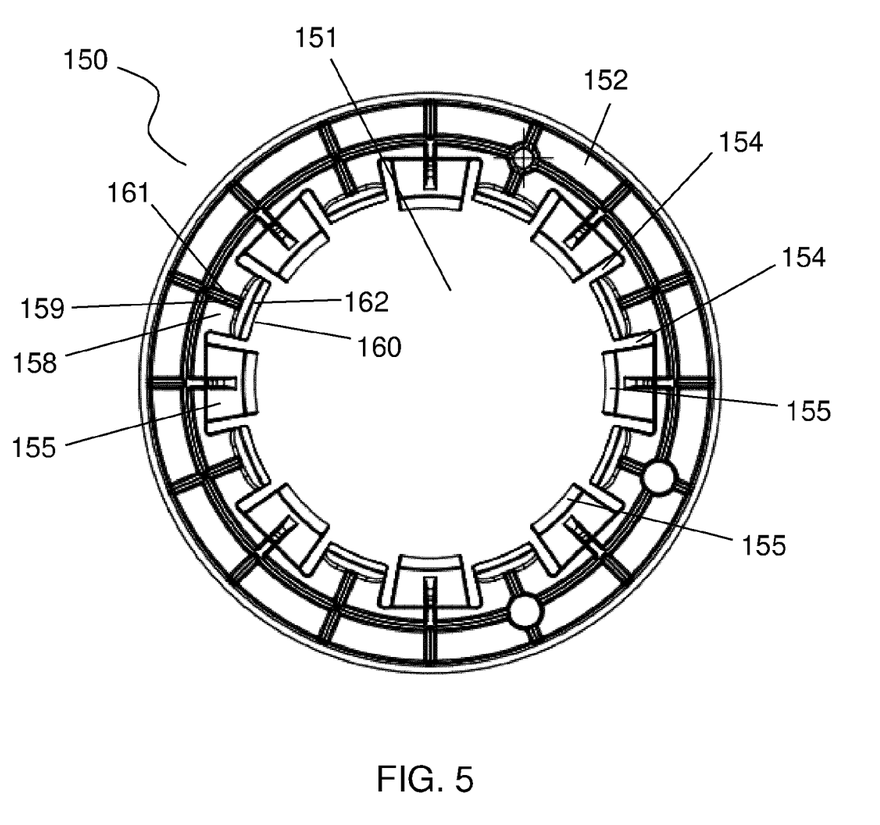
FIG. 5 shows an upper view of an embodiment of a connector ring.

FIG. 5 shows a top-down view of a connector ring (150) comprising an annular base (152) and a plurality of radially inwardly protruding flanges (153). Here every second radially inwardly protruding flange is an engagement flange (155) and every second radially inwardly protruding flange is a support flange (158). It can be seen that the radially inwardly protruding flanges (153) are separated by a gap (154) and wherein the gaps are formed along each radially inwardly protruding flange. Each support flange has a support structure (159), comprising at least one radially extending support element (161) and/or at least one edge support element (162) disposed along the inner support flange edge (160). In the shown example, the support structure comprises one radially extending support element (161) and one edge support element (162) disposed along the inner support flange edge (160). The support structures are arranged to provide the connector ring with an increased rigidity, and are generally stiff, preferably stiffer than the engagement flanges.

Figure 6A:
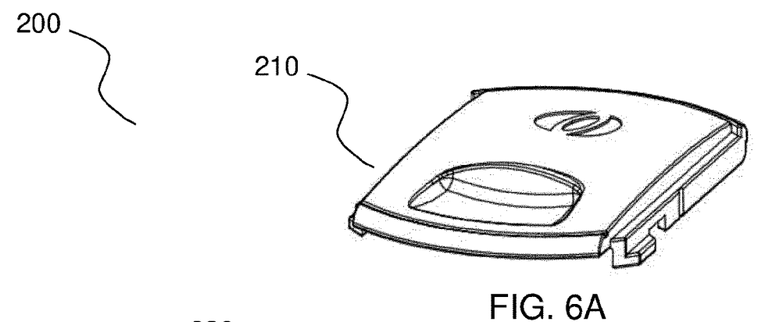
FIG. 6 shows an example of a lid for an ostomy implant.
Figure 6B:
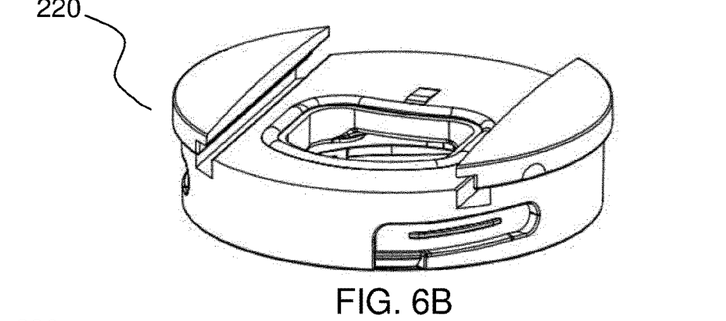
Figure 6C:
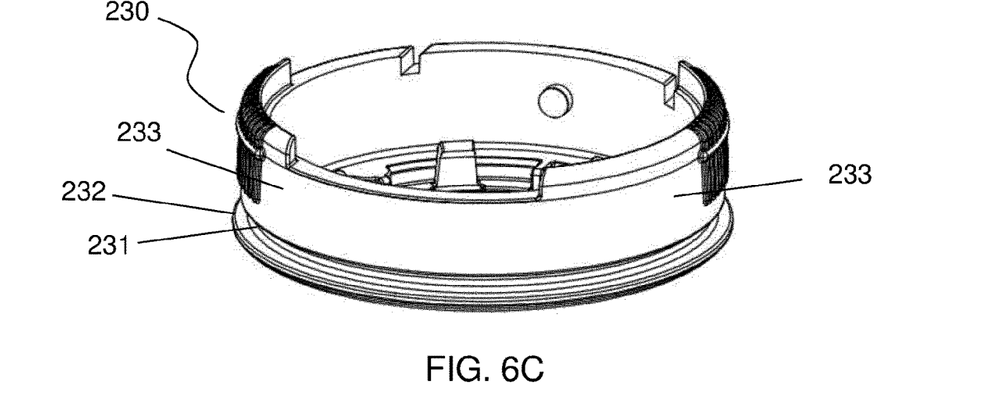

FIG. 6 shows a lid (200) for an ostomy implant. The lid (200) comprises a ring-shaped base part (230) adapted to engage with an open end of the ostomy implant, FIG. 6C. Further, the lid comprises a cap part (220) adapted to fit inside the ring-shaped base part, FIG. 6B, wherein the cap part is rotatable with respect to the ring-shaped base part to lock and unlock the lid to the ostomy implant, and wherein the cap part has a through-hole. The cap part further has a slider (210), FIG. 6A, configured to be radially slid into a recess of the cap part in a closed configuration, wherein the slider completely covers the through-hole of the cap part, and radially slid out from the recess in an open configuration, wherein the slider does not cover the through-hole of the cap part.

The lid (200) comprises connection means (231) in the form of a circumferential groove formed on an outer surface of the base part of the lid. Further, the lid comprises an outer circumferential ring (232). During use, the lid is attached to an ostomy implant and prevents leakage of waste from the stoma. For evacuation of the stoma, the user attaches the emptying device assembly (100) to the lid (200) by pushing the connector ring over the lid, such that at least the slider is moved inside the emptying device, i.e. into the compartment formed between the first film layer and the second film layer. Once the engagement flanges engage with the connection means of the lid, i.e. the circumferential groove (231), the emptying device assembly is attached to the lid (200). In this position, the support flanges may abut an outer circumferential ring (232) located below the circumferential groove (231), i.e. towards the user of the lid. In this position the engagement flanges and the support flanges provide support to the emptying device (110) and/or to the emptying device assembly (100), allowing for safe evacuation of the stoma.

Figure 7:
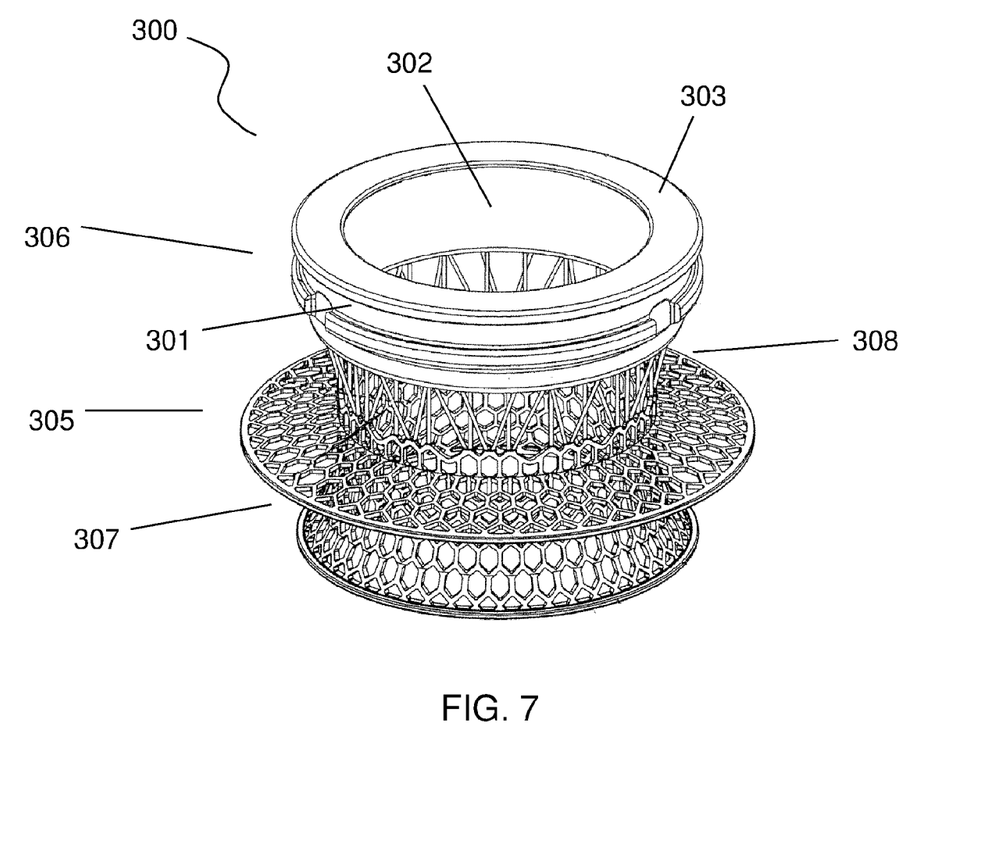
FIG. 7 shows an example of an ostomy implant.

FIG. 7 shows an example of an ostomy implant (300), the implant is formed of an interior section (305) and an exterior section (306). When implanted in a patient, the interior section (305) is located mostly or entirely inside the patient whereas the exterior section (306) is located mostly or entirely outside of the patient.

The interior section (305) comprises an inner interior section part (307) comprising substantially cylindrical structures formed of hexagonal mesh structures. The outer interior section part (308) connects the inner interior section part to the exterior section (306). The outer interior section part is formed from a number of rods arranged circumferentially around the implant extending between the inner interior section part and the exterior section.

The exterior section (306) is ring-shaped and comprises connection means (301) in the shape of an outer circumferential groove. The connector ring of the emptying device assembly (100) may be attached to the implant by pushing the connector ring onto the exterior section of the implant. Such that the open end (302) and the upper circumferential edge part of the implant protrudes into the compartment of the emptying device, formed between the first and the second film layer. The connector ring is engaged with the implant when the engagement flanges engage with the circumferential groove (301) of the implant. When the connection ring is pushed into the correct position for engagement with the implant, the engagement flanges snap into place into the circumferential groove (301). At this position the support flanges abut an outer surface of the implant, such as the outer circumferential ring (304), thereby providing increased support.

LIST OF ELEMENTS IN FIGURES

100—emptying device assembly
110—emptying device
111—first film layer
112—second film layer
113—peripheral part
114—first hole
115—notch
116—proximal end
117—distal end
118—truncated corner
119—annular attachment area
120—annular protection area
150—connector ring
151—second hole
152—annular base
153—radially inwardly protruding flanges
154—gap
155—engagement flange
156—hook element/guide element
157—inner engagement flange edge
158—support flange 159—support structure
160—inner support flange edge
161—radially extending support element
162—edge support element
200—lid
210—slider
220—cap part
230—base part
231—outer circumferential groove
232—outer circumferential ring
233—outer part
300—ostomy implant
301—circumferential groove
302—open end
303—upper circumferential edge part
305—interior section
306—exterior section
307—inner interior section part
308—outer interior section part Items 1. An emptying device assembly for evacuation of a stoma, comprising:
a first film layer and a second film layer, said first film layer and second film layer being attached along a peripheral part to form an emptying device, wherein the first film layer comprises a first hole; and
an integrated connector ring comprising:
an annular base defining a second hole concentric with the first hole, wherein the annular base is attached, such as welded, to the emptying device around the first hole;
a plurality of radially inwardly protruding flanges, wherein at least a subset of the protruding flanges are adapted to engage with an outer circumferential groove of a cylindrical ostomy implant or a lid of an ostomy implant.

2. The emptying device assembly according to item 1, wherein the integrated connector ring is adapted to form a fluid connection between the emptying device and the stoma.

3. The emptying device assembly according to any one of the preceding items, wherein the first film layer is elastic.

4. The emptying device assembly according to item 3, wherein the first hole is smaller than the second hole.

5. The emptying device assembly according to any one of the preceding items, wherein the annular base is attached, such as welded, to an annular attachment area of the first film layer.

6. The emptying device assembly according to item 5, wherein the first film layer comprises an annular protection area extending radially inwards relative to the annular attachment area, such as to overlap at least a part of the second hole.

7. The emptying device assembly according to item 6, wherein the annular protection area at least partially overlaps the second hole.

8. The emptying device assembly according to any one of items 5-7, wherein the annular protection area is arranged to, during use, protect, and/or form a seal against, an outer part of the implant or the lid.

9. The emptying device assembly according to any one of items 5-8, wherein the annular protection area extends radially inwards, such that it covers the flanges.

10. The emptying device assembly according to any one of items 9, wherein the annular protection area extends radially inwards, beyond the flanges, such as at least 5 mm beyond the edge of the flanges.

11. The emptying device assembly according to any one of the preceding items, wherein the first hole and the second hole are substantially circular, and/or wherein the first hole and the second hole are substantially concentric.

12. The emptying device assembly according to any one of the preceding items, wherein the plurality of radially inwardly protruding flanges are separated by gaps.

13. The emptying device assembly according to any one of the preceding items, wherein the plurality of radially inwardly protruding flanges comprise engagement flanges adapted to engage with an outer circumferential groove of a cylindrical ostomy implant or a lid of an ostomy implant.

14. The emptying device assembly according to item 13, wherein the engagement flanges are made of a resilient material.

15. The emptying device assembly according to any one of items 13-14, wherein the connector ring comprises restriction means, for restricting bending of one or more engagement flanges in a direction away from the second film layer.

16. The emptying device assembly according to item 15, wherein the restriction means comprises two adjacent protrusions arranged to restrict bending of the engagement flanges, in the direction of the protrusions.

17. The emptying device assembly according to any one of items 13-16, wherein each engagement flange has a hook element or a guide element at an inner engagement flange edge towards a center of the second hole.

18. The emptying device assembly according to item 17, wherein the hook element or guide element is dimensioned to fit into the circumferential groove of the cylindrical ostomy implant or the lid of the ostomy implant.

19. The emptying device assembly according to any one of the preceding items, wherein the plurality of radially inwardly protruding flanges comprise support flanges adapted to stabilize the integrated connector ring.

20. The emptying device assembly according to item 19, wherein the support flanges are generally stiff.

21. The emptying device assembly according to any one of items 19-20, wherein each support flange has an inner support flange edge towards a center of the second hole, wherein the support flange is dimensioned such that the inner support flange edge abuts an outer circumferential ring of the cylindrical ostomy implant or the lid of the ostomy implant.

22. The emptying device assembly according to any one of items 19-21, wherein each support flange has a support structure.

23. The emptying device assembly according to item 22, wherein the support structure comprises at least one radially extending support element and/or at least one edge support element disposed along the inner support flange edge.

24. The emptying device assembly according to any one of items 13-18 and any one of items 19-23, wherein every second radially inwardly protruding flange is an engagement flange and every second radially inwardly protruding flange is a support flange.

25. The emptying device assembly according to any one of items 13-18 and any one of items 19-24, wherein the engagement flanges protrude more than the support flanges.

26. The emptying device assembly according to any one of items 13-18 and any one of items 19-25, wherein the support flanges are stiffer than the engagement flanges.

27. The emptying device assembly according to any one of the preceding items, wherein the emptying device has a tapered shape, preferably a substantially flat, tapered shape.

28. The emptying device assembly according to item 27, wherein the emptying device has a shape of a triangle with one truncated corner.

29. The emptying device assembly according to any one of the preceding items, wherein the emptying device is an open-ended emptying sleeve.

30. The emptying device assembly according to any one of items 1-28, wherein the emptying device is an emptying pouch.

31. The emptying device assembly according to item 30, wherein the emptying pouch comprises a perforation and/or one or more notches for opening one end of the emptying pouch.

32. A method of manufacturing an emptying device assembly according to any one of the preceding items, the method comprising the steps of (in any order):
  forming a first circular hole in the first film layer;
  attaching a first film layer and a second film layer along peripheral parts of the layers to form a sleeve or pouch;
  attaching a connector ring to the first film layer around the first hole, wherein the connector ring comprises:
    an annular base defining a second hole concentric with the first hole; and
    a plurality of radially inwardly protruding flanges, wherein at least a subset of the protruding flanges are adapted to engage with an outer circumferential groove of a cylindrical ostomy implant or a lid of an ostomy implant.

33. The method according to item 32, wherein the emptying device assembly is arranged according to any one of items 1-31.

34. A connector ring for attachment of a further device to an ostomy implant or a lid of an ostomy implant, the connector ring comprising:
  an annular base defining a connector hole; and
  a plurality of radially inwardly protruding flanges, wherein at least a subset of the protruding flanges are adapted to engage with an outer circumferential groove of a cylindrical ostomy implant or a lid of an ostomy implant.

35. The connector ring according to item 34, wherein the connector ring comprises attachment means for attachment of the further device to the connector ring.

36. The connector ring according to any one of items 34-35, wherein the connector ring forms an integral part of the further device.

37. The connector ring according to any one of items 34-39, wherein the connector ring forms an integral part of the further device.

38. The connector ring according to any one of items 34-40, wherein the integrated connector ring is adapted to form a fluid connection between the further device and the stoma.

39. The connector ring according to any one of items 34-41, wherein the connector hole is substantially circular.

40. The connector ring according to any one of items 34-44, wherein the plurality of radially inwardly protruding flanges are separated by gaps.

41. The connector ring according to any one of items 34-45, wherein the plurality of radially inwardly protruding flanges comprise engagement flanges adapted to engage with an outer circumferential groove of a cylindrical ostomy implant or a lid of an ostomy implant.

42. The connector ring according to item 41, wherein the connector ring comprises restriction means, for restricting bending of one or more engagement flanges in a direction away from the second film layer.

43. The connector ring according to item 42, wherein the restriction means comprises two adjacent protrusions arranged to restrict bending of the engagement flanges, in the direction of the protrusions.

44. The connector ring according to any one of items 41-43, wherein the engagement flanges are made of a resilient material.

45. The connector ring according to any one of items 41-44, wherein each engagement flange has a hook element or a guide element at an inner engagement flange edge towards a center of the second hole.

46. The connector ring according to item 45, wherein the hook element or guide element is dimensioned to fit into the circumferential groove of the cylindrical ostomy implant or the lid of the ostomy implant.

47. The connector ring according to any one of items 34-46, wherein the plurality of radially inwardly protruding flanges comprise support flanges adapted to stabilize the integrated connector ring.

48. The connector ring according to item 47, wherein the support flanges are generally stiff.

49. The connector ring according to any one of items 47-48, wherein each support flange has an inner support flange edge towards a center of the second hole, wherein the support flange is dimensioned such that the inner support flange edge abuts an outer circumferential ring of the cylindrical ostomy implant or the lid of the ostomy implant.

50. The connector ring according to any one of items 47-49, wherein each support flange has a support structure.

51. The connector ring according to item 50, wherein the support structure comprises at least one radially extending support element and/or at least one edge support element disposed along the inner support flange edge.

52. The connector ring according to any one of items 41-46 and any one of items 47-51, wherein every second radially inwardly protruding flange is an engagement flange and every second radially inwardly protruding flange is a support flange.

53. The connector ring according to any one of items 41-46 and any one of items 47-52, wherein the engagement flanges protrude more than the support flanges.

54. The connector ring according to any one of items 41-46 and any one of items 47-53, wherein the support flanges are stiffer than the engagement flanges.

55. The connector ring according to any one of items 34-54, wherein the connector ring is arranged according to the connector ring of any one of items 1-31.

56. Use of a connector ring according to any one of items 34-54 for attachment of a further device to an ostomy implant or a lid of an ostomy implant.

57. The use according to item 56, wherein the further device is an ostomy bag, a catheter or a sleeve, such as an emptying sleeve or an irrigation sleeve.

58. The use according to any one of items 56-57, wherein the connector ring forms an integral part of the further device.

The invention claimed is:
1. An emptying device assembly for evacuation of a stoma, comprising:
  a first film layer and a second film layer, said first film layer and second film layer being attached along a peripheral part to form an emptying device, wherein the first film layer comprises a first hole; and an integrated connector ring comprising:
  an annular base defining a second hole concentric with the first hole, wherein the annular base is attached to an annular attachment area of the first film layer around the first hole;
  a plurality of radially inwardly protruding flanges, wherein at least a subset of the protruding flanges are adapted to engage with an outer circumferential groove of a cylindrical ostomy implant or a lid of an ostomy implant.

2. The emptying device assembly according to claim 1, wherein the first film layer is elastic and wherein the first hole is smaller than the second hole.

3. The emptying device assembly according to claim 1, wherein the emptying device assembly comprises an annular protection area arranged to, during use, decrease leakages or form a seal to the ostomy implant or the lid of an ostomy implant.

4. The emptying device assembly according to claim 1, wherein the annular protection area is formed by the first film layer extending radially inwards from the annular attachment area, or wherein the annular protection area extends radially inwards and extends beyond the radially inner edges of the flanges.

5. The emptying device assembly according to claim 1, wherein the plurality of radially inwardly protruding flanges comprise engagement flanges adapted to engage with an outer circumferential groove of a cylindrical ostomy implant or a lid of an ostomy implant; and wherein the engagement flanges are made of a resilient material.

6. The emptying device assembly according to claim 5, wherein the connector ring comprises a restrictor, for restricting bending of at least one of the engagement flanges in an outwards direction away from the second film layer; while said at least one engagement flange is not restricted by the restrictor to be bent in an inwards direction towards the second film layer.

7. The emptying device assembly according to claim 6, wherein the restrictor comprises two adjacent protrusions arranged to restrict bending of at least one engagement flange, in the direction of the protrusions, or wherein each engagement flange comprises a hook element or a guide element at an inner engagement flange edge towards a center of the second hole.

8. The emptying device assembly according to claim 1, wherein the plurality of radially inwardly protruding flanges comprise support flanges adapted to stabilize the integrated connector ring.

9. The emptying device assembly according to claim 8, wherein each support flange has an inner support flange edge towards a center of the second hole, and wherein the support flange is dimensioned such that the inner support flange edge abuts an outer circumferential ring of the cylindrical ostomy implant or the lid of the ostomy implant, or wherein each support flange has a support structure.

10. The emptying device assembly according claim 5, wherein the plurality of radially inwardly protruding flanges comprise support flanges adapted to stabilize the integrated connector ring.

11. A method of manufacturing an emptying device assembly according to claim 1, the method comprising the steps of:
  forming a first circular hole in the first film layer;
  attaching the first film layer and the second film layer along peripheral parts of the layers to form a sleeve or pouch;
  attaching a connector ring to the first film layer around the first hole, wherein the connector ring comprises:
    an annular base defining a second hole concentric with the first hole; and
    a plurality of radially inwardly protruding flanges, wherein at least a subset of the protruding flanges are adapted to engage with an outer circumferential groove of a cylindrical ostomy implant or a lid of an ostomy implant.

12. A connector ring for attachment of a further device to an ostomy implant or a lid of an ostomy implant, the connector ring comprising:
  an annular base defining a connector hole; and
  a plurality of radially inwardly protruding flanges, wherein at least a subset of the protruding flanges are adapted to engage with an outer circumferential groove of a cylindrical ostomy implant or a lid of an ostomy implant.

13. The connector ring according to claim 12, wherein the plurality of radially inwardly protruding flanges are separated by gaps.

14. The connector ring according to claim 12, wherein the plurality of radially inwardly protruding flanges comprise engagement flanges adapted to engage with an outer circumferential groove of a cylindrical ostomy implant or a lid of an ostomy implant.

15. The connector ring according to claim 14, wherein the connector ring comprises a restrictor, for restricting bending of one or more engagement flanges in a first direction but allowing bending of the engagement flanges in a direction opposite to the first direction.

16. The connector ring according to claim 12, wherein the plurality of radially inwardly protruding flanges comprise support flanges adapted to stabilize the connector ring during use.

17. The connector ring according to claim 16, wherein each support flange has an inner support flange edge towards a center of the connector hole, wherein the support flange is dimensioned such that the inner support flange edge is arranged to abut an outer circumferential ring of the cylindrical ostomy implant or the lid of the ostomy implant; or wherein each support flange has a support structure adapted to increase the structural rigidity of the connector ring.

18. The connector ring according to claim 14, wherein the plurality of radially inwardly protruding flanges further comprise support flanges adapted to stabilize the connector ring during use.

19. The connector ring according to claim 18, wherein the engagement flanges protrude more than the support flanges.

20. The connector ring according to claim 18, wherein the support flanges are stiffer than the engagement flanges.

* * * * *